United States Patent
Peine et al.

(10) Patent No.: US 12,144,572 B2
(45) Date of Patent: Nov. 19, 2024

(54) ROBOTIC SURGICAL SYSTEMS WITH ROLL, PITCH, AND YAW REALIGNMENT INCLUDING TRIM AND FLIP ALGORITHMS

(71) Applicant: Covidien LP, Mansfield, MA (US)

(72) Inventors: William Peine, Ashland, MA (US); Albert Dvornik, Somerville, MA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/228,935

(22) Filed: Aug. 1, 2023

(65) Prior Publication Data

US 2023/0372040 A1 Nov. 23, 2023

Related U.S. Application Data

(63) Continuation of application No. 16/643,247, filed as application No. PCT/US2018/049330 on Sep. 4, 2018, now Pat. No. 11,717,362.

(Continued)

(51) Int. Cl.
*A61B 34/35* (2016.01)
*A61B 17/00* (2006.01)
*A61B 34/00* (2016.01)

(52) U.S. Cl.
CPC .... *A61B 34/35* (2016.02); *A61B 2017/00199* (2013.01); *A61B 2034/742* (2016.02); *A61B 2034/76* (2016.02)

(58) Field of Classification Search
CPC ... A61B 34/35; A61B 34/37; A61B 2034/742; A61B 2034/743; A61B 2034/744; A61B 34/76; A61B 34/77; A61B 2017/00199

(Continued)

(56) References Cited

U.S. PATENT DOCUMENTS 7,695,481 B2 4/2010 Wang et al.
8,828,023 B2 9/2014 Neff et al.
(Continued)

FOREIGN PATENT DOCUMENTS

CN 102470015 A 5/2012
WO 2016053657 A1 4/2016
(Continued)

OTHER PUBLICATIONS

Indian Office Action dated Dec. 26, 2022 corresponding to counterpart Patent Application IN 202017008955.

(Continued)

*Primary Examiner* — Aaron F Roane
(74) *Attorney, Agent, or Firm* — Carter, DeLuca & Farrell LLP

(57) ABSTRACT

A robotic surgical system or simulator includes an input device, a display device, and a processing unit. The display device includes a representation of a surgical tool that is operably associated with the input device. The processing unit is in communication with the input device and is associated with the representation of a surgical tool to rotate the representation about a first axis of movement based on a scaled rotation of the input device about a first axis of rotation. In an aligned configuration, the input device is aligned with the representation about the first axis of rotation. When the input device is misaligned with the representation, the processing unit varies the scaled rotation of the input device to return the input device to the first aligned configuration until the input device is misaligned about the first axis of rotation a first predetermined offset from the aligned configuration.

17 Claims, 3 Drawing Sheets

Related U.S. Application Data

(60) Provisional application No. 62/554,292, filed on Sep. 5, 2017.

(58) Field of Classification Search
USPC .......................................................... 606/1
See application file for complete search history.

(56) References Cited

U.S. PATENT DOCUMENTS

| | | |
|---|---|---|
| 9,696,700 B2 | 7/2017 | Beira et al. |
| 10,278,783 B2 | 5/2019 | Itkowitz et al. |
| 11,717,362 B2 | 8/2023 | Peine et al. |
| 2011/0276058 A1 | 11/2011 | Choi et al. |
| 2014/0107471 A1 | 4/2014 | Haider et al. |
| 2017/0112582 A1 | 4/2017 | Itkowitz et al. |
| 2018/0014897 A1 | 1/2018 | Peine |
| 2018/0036088 A1* | 2/2018 | Kilroy .................. A61B 34/74 |
| 2018/0310999 A1 | 11/2018 | Peine |

FOREIGN PATENT DOCUMENTS

| | | |
|---|---|---|
| WO | 2016133633 A1 | 8/2016 |
| WO | 2017100434 A1 | 6/2017 |

OTHER PUBLICATIONS

Japanese Office Action dated Aug. 12, 2022 corresponding to counterpart Patent Application JP 2020-513334.

International Search Report dated Dec. 19, 2018 and Written Opinion completed Dec. 19, 2018 corresponding to counterpart Int'l Patent Application PCT/2018/049330.

Extended European Search Report dated Apr. 22, 2021 corresponding to counterpart Patent Application EP 18853724.5.

Chinese First Office Action dated Jan. 31, 2023 corresponding to counterpart Patent Application CN 201880006817.6.

* cited by examiner

ROBOTIC SURGICAL SYSTEMS WITH ROLL, PITCH, AND YAW REALIGNMENT INCLUDING TRIM AND FLIP ALGORITHMS

CROSS-REFERENCE TO RELATED APPLICATIONS

This application is a Continuation Application which claims the benefit of and priority to U.S. patent application Ser. No. 16/643,247, filed Feb. 28, 2020, which is a U.S. National Stage Application filed under 35 U.S.C. § 371(a) of International Patent Application Serial No. PCT/US2018/049330, filed Sep. 4, 2018, which claims the benefit of and priority to U.S. Provisional Patent Application Ser. No. 62/554,292, filed Sep. 5, 2017, the entire disclosure of which is incorporated by reference herein.

BACKGROUND

Robotic surgical systems have been used in minimally invasive medical procedures. During a medical procedure, the robotic surgical system is controlled by a surgeon interfacing with a user interface. The user interface allows the surgeon to manipulate an end effector that acts on a patient. The user interface includes an input controller or handle that is moveable by the surgeon to control the robotic surgical system.

Robotic surgical systems typically used a scaling factor to scale down the motions of the surgeons hands to determine the desired position of the end effector within the patient so that the surgeon could more precisely move the end effector inside the patient. However, the larger the scaling factor, the farther the surgeon had to move the input device handle to move the end effector the same distance. Since the input device handle has a fixed range of motion, this meant that for larger scaling factors the surgeon may have reached an end of the range of motion of an input handle more often.

In addition, during a medical procedure a surgeon needs to rotate the end effector about a roll axis, a pitch axis, and a yaw axis to properly position the end effector to act on tissue. Further, during a medical procedure, clutching of movement of the input handle relative to the input handle may cause the input handle to become misaligned with the end effector about one or more of the roll axis, the pitch axis, and/or the yaw axis.

There is a continuing need for a robotic surgical system that realigns the input handle with the end effector during a medical procedure.

SUMMARY

This disclosure generally relates to the scaling of movement of an input device of a user interface to movement of a tool of a robotic system during a surgical procedure about one or more of roll, pitch, and yaw axis including a "trim" and/or a "flip" algorithm.

In an aspect of the present disclosure, a robotic surgical system or simulator includes an input device, a display device, and a processing unit. The input device is rotatable about a first axis of rotation. The display device includes a representation of a surgical tool that is operably associated with the input device. The processing unit is in communication with the input device and is operatively associated with the representation of a surgical tool to rotate the representation of a surgical tool about a first axis of movement based on a scaled rotation of the input device about the first axis of rotation. The input device has an aligned configuration in which the input device is aligned with the representation of a surgical tool about the first axis of rotation. When the input device is misaligned with the representation of a surgical tool about the first axis of rotation, the processing unit varies the scaled rotation of the input device about the first axis of rotation to return the input device to the first aligned configuration until the input device is misaligned about the first axis of rotation by a first predetermined offset from the aligned configuration. The first predetermined offset may be in a range of about 5° to about 45°.

In aspects, the input device is rotatable about a second axis of rotation that is perpendicular to the first axis of rotation. The processing unit may be in communication with the input device and may be operably associated with the representation of a surgical tool to rotate the representation of a surgical tool about a second axis of movement based on a scaled rotation of the input device about the second axis of rotation. In the aligned configuration, the input device is aligned with the representation of a surgical tool about the second axis of rotation. When the input device is misaligned with the representation of a surgical tool about the second axis of rotation, the processing unit varies the scaled rotation of the input device about the second axis of rotation to return the input device to the aligned configuration until the input device is misaligned about the second axis of rotation a second predetermined offset from the aligned configuration. The first predetermined offset may be equal to the second predetermined offset. Alternatively, the first predetermined offset may be greater or less than the second predetermined offset. For example, the first predetermined offset may be in a range of about 16° to about 45° and the second predetermined offset may be in a range of about 5° to about 15°.

In some aspects, the input device is rotatable about a third axis of rotation that is perpendicular to the first and second axes of rotation. The processing unit may be in communication with the input device and may be operably associated with the representation of a surgical tool to rotate the representation of a surgical tool about a third axis of movement based on a scaled rotation of the input device about the third axis of rotation. In the aligned configuration the input device is aligned with the representation of a surgical tool about the third axis of rotation. When the input device is misaligned with the representation of a surgical tool about the third axis of rotation, the processing unit varies the scaled rotation of the input device about the third axis of rotation to return the input device to the aligned configuration until the input device is misaligned about the third axis of rotation a third predetermined offset from the aligned configuration.

In particular aspects, the first predetermined offset is equal to each of the second and third predetermined offsets. Alternatively, the first predetermined offset may be greater or less than the second or third predetermined offsets. Additionally, the second predetermined offset may be greater or less than the second predetermined offset. The first, second, and/or third predetermined offset may be selectable by a user. Additionally or alternatively, the first, second, and/or third predetermined offsets may be at least partially determined based on the representation of a tool. When the input device is misaligned with the representation of a surgical tool about the first, second, and/or third axis of rotation by an amount greater than a predetermined misalignment, the aligned configuration about a respective one of the first, second, and/or third axis of rotation may be flipped 180° about the respective axis of rotation.

In another aspect of the present disclosure, a method of operating a surgical robot or surgical simulator includes a processing unit receiving a rotation of an input device of a robotic surgical system about a first axis of rotation and scaling the rotation of the input device to a rotation of a representation of a tool on a display device about a first axis of movement. The processing unit scales down rotation of the input device when the input device is moved away from an aligned configuration to realign the input device with the representation of a tool until the input device is within a predetermined offset with the representation of a tool about the first axis of rotation.

In aspects, scaling rotation of the input device to the rotation of the representation of a tool on the display device includes the processing unit scales up rotation of the input device when the input device is moved towards the aligned configuration to realign the input device with the representation of a tool until the input devices is within the predetermined offset with the representation of a tool about the first axis of rotation. The method may include selecting the predetermined offset. Additionally or alternatively, selecting the predetermined offset may include the processing unit determining the predetermined offset based on the representation of a tool.

In some aspects, the method includes flipping the aligned configuration of the input device 180° about the first axis of rotation when the input device is misaligned with the representation of the tool greater than a predetermined misalignment.

Further details and aspects of exemplary embodiments of the present disclosure are described in more detail below with reference to the appended figures.

BRIEF DESCRIPTION OF THE DRAWINGS

Various aspects of the present disclosure are described herein below with reference to the drawings, which are incorporated in and constitute a part of this specification, wherein.

DETAILED DESCRIPTION

Figure 1:
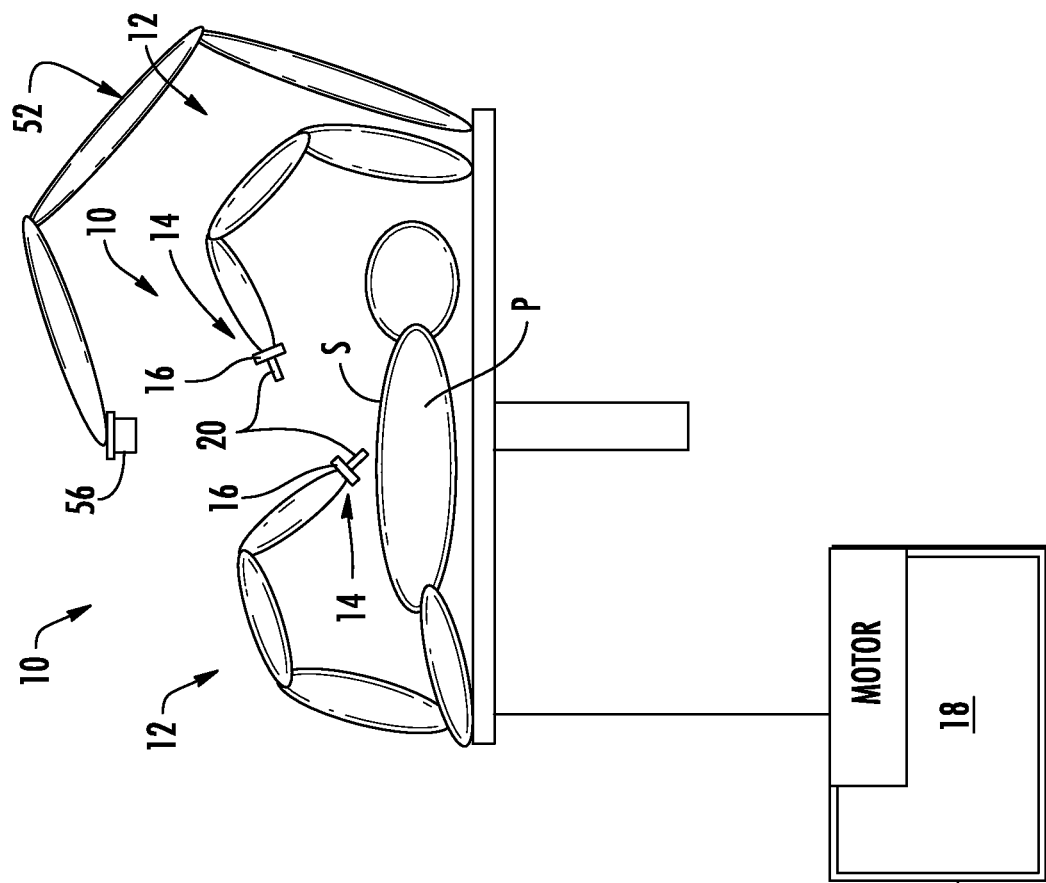
FIG. 1 is a schematic illustration of an user interface and a robotic system in accordance with the present disclosure.
Figure 1:
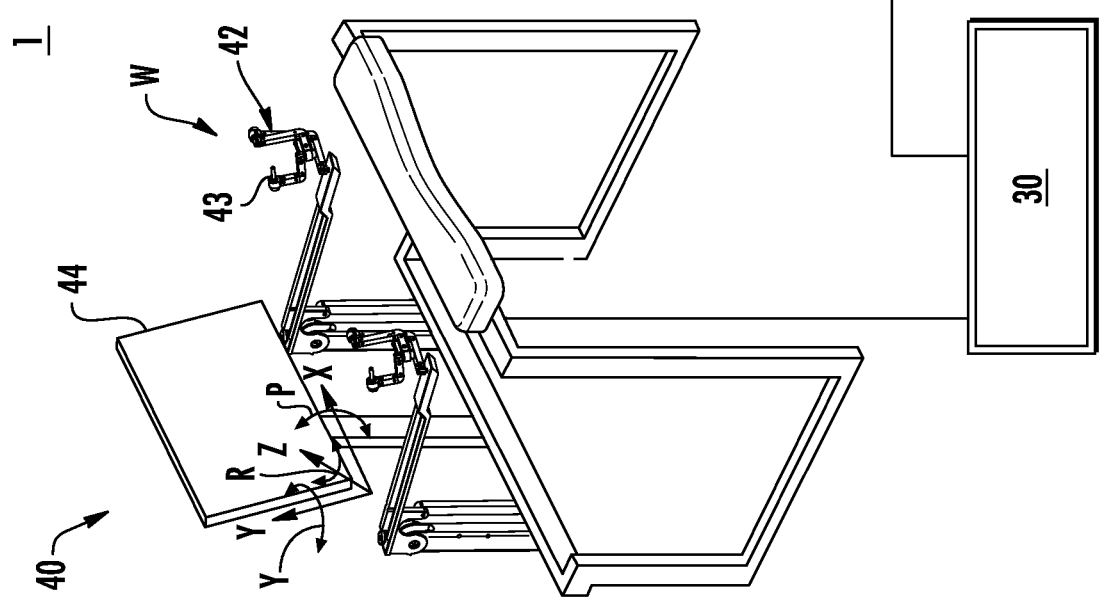

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician. In addition, as used herein the term "neutral" is understood to mean non-scaled.

This disclosure generally relates to the scaling of movement of an input device of a user interface for movement of a tool of a robotic system during a surgical procedure. In particular, this disclosure relates to the scaling of movement about a roll axis, a pitch axis, and a yaw axis of the tool. The robotic system includes an alignment algorithm configured to realign the input device of a user interface with the position of the tool about one or more of the roll, pitch, and yaw axes. In addition, the robotic system may include a "trim" algorithm that allows the input device to remain offset at a predetermined offset about one or more of the roll, pitch, and yaw axes instead of fully aligning the input device about each of the roll, pitch, and yaw axes. Additionally or alternatively, the robotic system may include a "flip" algorithm that rotates an aligned configuration of the input device relative to the tool 180° about a respective one of the roll, pitch, and yaw axes when the input device is misaligned greater than a predetermined misalignment about a respective one of the roll, pitch, and yaw axes.

Referring to FIG. 1, a robotic surgical system 1 in accordance with the present disclosure is shown generally as a robotic system 10, a processing unit 30, and a user interface 40. The robotic system 10 generally includes linkages 12 and a robot base 18. The linkages 12 moveably support an end effector or tool 20 which is configured to act on tissue. The linkages 12 may be in the form of arms each having an end 14 that supports an end effector or tool 20 which is configured to act on tissue. In addition, the ends 14 of the arms 12 may include an imaging device 16 for imaging a surgical site "S". The user interface 40 is in communication with robot base 18 through the processing unit 30.

The user interface 40 includes a display device 44 which is configured to display three-dimensional images. The display device 44 displays three-dimensional images of the surgical site "S" which may include data captured by imaging devices 16 positioned on the ends 14 of the arms 12 and/or include data captured by imaging devices that are positioned about the surgical theater (e.g., an imaging device positioned within the surgical site "S", an imaging device positioned adjacent the patient "P", imaging device 56 positioned at a distal end of an imaging arm 52). The imaging devices (e.g., imaging devices 16, 56) may capture visual images, infra-red images, ultrasound images, X-ray images, thermal images, and/or any other known real-time images of the surgical site "S". The imaging devices transmit captured imaging data to the processing unit 30 which creates three-dimensional images of the surgical site "S" in real-time from the imaging data and transmits the three-dimensional images to the display device 44 for display.

The user interface 40 also includes input handles 42 which are supported on control arms 43 which allow a clinician to manipulate the robotic system 10 (e.g., move the arms 12, the ends 14 of the arms 12, and/or the tools 20). Each of the input handles 42 is in communication with the processing unit 30 to transmit control signals thereto and to receive feedback signals therefrom. Additionally or alternatively, each of the input handles 42 may include input devices 46 (FIG. 2) which allow the surgeon to manipulate (e.g., clamp, grasp, fire, open, close, rotate, thrust, slice, etc.) the tools 20 supported at the ends 14 of the arms 12.

Figure 2:
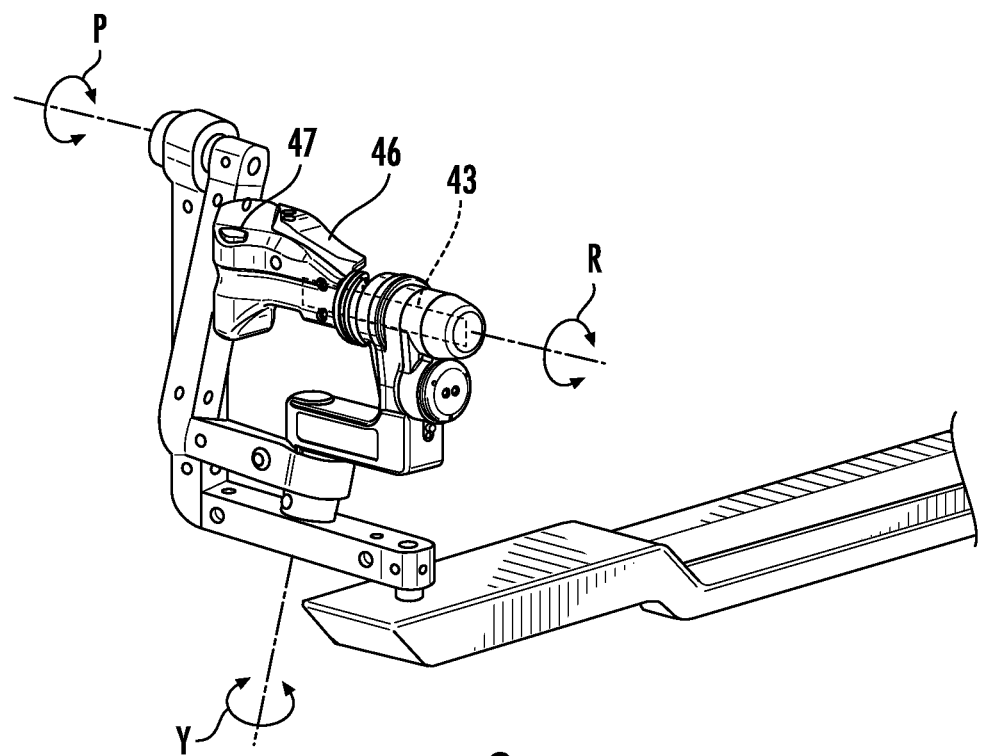
FIG. 2 is a perspective view of a input device supported on an end of a control arm of the user interface of FIG. 1.

With additional reference to FIG. 2, each of the input handles 42 is moveable through a predefined workspace to move the ends 14 of the arms 12, e.g., tools 20, within a surgical site "S". The three-dimensional images on the display device 44 are orientated such that the movement of the input handles 42 move the ends 14 of the arms 12 as viewed on the display device 44. The three-dimensional images remain stationary while movement of the input handles 42 is scaled to movement of the ends 14 of the arms 12 within the three-dimensional images. To maintain an orientation of the three-dimensional images, kinematic mapping of the input handles 42 is based on a camera orientation relative to an orientation of the ends 14 of the arms 12. The orientation of the three-dimensional images on the display device 44 may be mirrored or rotated relative to view from above the patient "P". In addition, the size of the three-dimensional images on the display device 44 may be scaled to be larger or smaller than the actual structures of the surgical site permitting a clinician to have a better view of structures within the surgical site "S". As the input handles 42 are moved, the tools 20 are moved within the surgical site "S" as detailed below. Movement of the tools 20 may also include movement of the ends 14 of the arms 12 which support the tools 20.

For a detailed discussion of the construction and operation of a robotic surgical system 1, reference may be made to U.S. Pat. No. 8,828,023, the entire contents of which are incorporated herein by reference.

As detailed above, the user interface 40 is in operable communication with the robotic system 10 to perform a surgical procedure on a patient; however, it is envisioned that the user interface 40 may be in operable communication with a surgical simulator (not shown) to virtually actuate a robotic system and/or tool in a simulated environment. For example, the robotic surgical system 1 may have a first mode in which the user interface 40 is coupled to actuate the robotic system 10 and a second mode in which the user interface 40 is coupled to the surgical simulator to virtually actuate a robotic system. The surgical simulator may be a standalone unit or be integrated into the processing unit 30. The surgical simulator virtually responds to a clinician interfacing with the user interface 40 by providing visual, audible, force, and/or haptic feedback to a clinician through the user interface 40. For example, as a clinician interfaces with the input handles 42, the surgical simulator moves representative tools that are virtually acting on tissue. It is envisioned that the surgical simulator may allow a clinician to practice a surgical procedure before performing the surgical procedure on a patient. In addition, the surgical simulator may be used to train a clinician on a surgical procedure. Further, the surgical simulator may simulate "complications" during a proposed surgical procedure to permit a clinician to plan a surgical procedure.

The movement of the tools 20 is scaled relative to the movement of the input handles 42. When the input handles 42 are moved within a predefined workspace, the input handles 42 send control signals to the processing unit 30. The processing unit 30 analyzes the control signals to move the tools 20 in response to the control signals. The processing unit 30 transmits scaled control signals to the robot base 18 to move the tools 20 in response to the movement of the input handles 42. The processing unit 30 scales the control signals by dividing an Input$_{distance}$ (e.g., the distance moved by one of the input handles 42) by a scaling factor $S_F$ to arrive at a scaled Output distance (e.g., the distance that one of the ends 14 is moved). The scaling factor $S_F$ is in a range between about 1 and about 10 (e.g., 3). This scaling is represented by the following equation:

$$Output_{distance} = Input_{distance}/S_F$$

It will be appreciated that the larger the scaling factor $S_F$ the smaller the movement of the tools 20 relative to the movement of the input handles 42.

For a detailed description of scaling movement of the input handle 42 along the X, Y, and Z coordinate axes to movement of the tool 20, reference may be made to commonly owned International Patent Application Serial No. PCT/US2015/051130, filed on Sep. 21, 2015, and entitled "Dynamic Input Scaling for Controls of Robotic Surgical System," and International Patent Application No. PCT/US2016/14031, filed Jan. 20, 2016, the entire contents of each of these disclosures is herein incorporated by reference.

Figure 3:
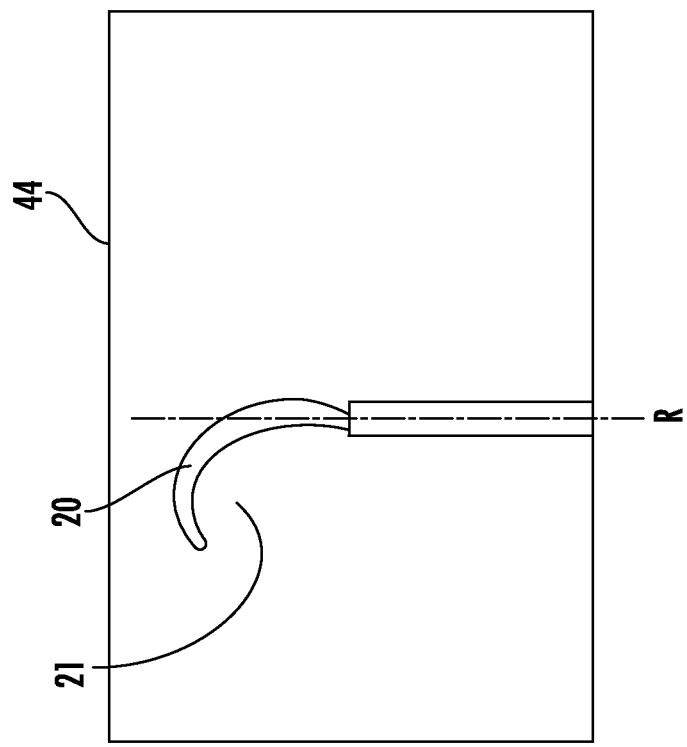
FIG. 3 is a view of a display device of the robotic system of FIG. 1 illustrating a representation of a tool within a surgical site while in a first position.

Referring also to FIGS. 2 and 3, the rotation of the input device 46 relative to each of the X, Y, and Z coordinate axes may be scaled to rotation of the tool 20 about a roll axis "R", a pitch axis "P", and a yaw axis "Y" (RPY). The roll axis "R" is aligned with an end effector of a tool, e.g., tool 20, as displayed on the display device 44 while pitch and yaw axes "P", "Y" are orientated to the camera frame as displayed on the display device 44 such that motions of the handles 42 and/or input device 46 are relative to a clinician's view of the display device 44. Specifically, the pitch axis "P" is about the X coordinate axis and the yaw axis "Y" is about the Y coordinate axis of a neutral frame of the handle. The scaling of rotation of the input device 46 about each of the RPY axes may be scaled up, down, or neutral manner. By scaling rotation up, a clinician is able to reduce rotation of the input device 46 about a particular one of the RPY axes to achieve a desired rotation of the tool 20 about the respective RPY axis. This up scaling may allow a clinician to have dexterity beyond a natural movement of the human body. For example, a clinician may roll a tool 20 beyond what is possible with the movement of the clinician's wrist without releasing the input device 46. In contrast, by scaling rotation down, a clinician is able to more precisely control rotation of the tool 20 about a particular one of the RPY axes of the tool 20 in response to rotation of the input device 46.

Rotation of the input device 46 about each of the RPY axes may be scaled in a different manner to rotation of the tool 20. For example, rotation of the input device 46 about the control shaft 43, i.e., rotation about the roll axis "R", may be scaled up, rotation of the input device 46 about the pitch axis "P" may be scaled in a neutral manner, and rotation of the input device 46 about the yaw axis "Y" may be scaled down. Any other combinations of scaling are contemplated herein and form a part of the present disclosure.

During a surgical procedure, rotation of the input device 46 may be "clutched" relative to rotation of the tool 20 about the RPY axes. The "clutching" of the input device 46 relative to the tool 20 may be manually selected by a clinician or may be automatically selected by the robotic surgical system 1. When input device 46 is reassociated or "declutched" with rotation of the tool 20 about the RPY axes, the input device 46 may be misaligned with the orientation of the tool 20 about one or more of the RPY axes.

The robotic surgical system 1 may vary the RPY scaling factors to realign the input device 46 with the tool 20 in a manner which is imperceptible to a clinician engaged with the input device 46. To realign the input device 46 with the tool 20 the RPY scaling factors in a direction away from an aligned or centered position may be scaled down more than when the clinician moves the input handle 46 towards the aligned configuration until the tool is aligned with the input device 46. By scaling down movement of the input handle 46 as the input handle 46 is moved towards the aligned configuration, the robotic surgical system 10 allows the input device 46 to "catch up" to the position of the tool 20 in a manner which is indiscernible to a clinician interfacing with the input device 46. For example, one or more of the RPY scaling factors may be increased in a range of about 5% to about 200% (e.g., 25% or 50%) when the input device 46 is moved away from the aligned configuration and the RPY scaling factor may remain unchanged when the input device 46 is moved towards the aligned configuration. Additionally or alternatively, one or more of the RPY scaling factors may be reduced in a range of about 5% to about 200% (e.g., 25% or 50%) when the input device 46 is moved towards the aligned configuration which causes the tool 20 to catch up with the position of the input device 46. When the tool 20 is aligned with the input device 46, the RPY scaling factors return to operating in a symmetrical manner which may be up, down, or neutral, e.g., have the same scaling factor. It will be appreciated that by scaling movement of the input device 46 relative to the tool 20 in this manner, the tool 20 remains stationary when the input device 46 is stationary and tool 20 only moves in response to a clinician moving the input device 46.

In an embodiment, the RPY scaling factors may vary based on the amount of misalignment of the respective RPY axis. For example, when the roll axis "R" is misaligned about 15 degrees, the scaling factor of the roll axis "R" may be scaled down about 10% for movement of the input device 46 towards the aligned configuration, and when the roll axis "R" is misaligned about 30 degrees, the roll axis "R" may be scaled down about 20% for movement of the input device 46 towards the aligned configuration. It is contemplated that the varying of the scaling factors may be a linear, exponential, polynomial, linear step, or other mathematical relationship. For a detailed description of varying scaling factors based on a distance or amount of misalignment, reference can be made to International Patent Application No. PCT/US16/14031, filed Jan. 20, 2016, the entire contents of which are hereby incorporated by reference.

In some embodiments, the robotic surgical system 1 may vary the RPY scaling factors to realign the input device 46 with the tool 20 until the misalignment of the input device 46 with the tool 20 is at or within a predetermined offset. For example, the input device 46 may be misaligned with the tool 20 about a roll axis by 100°. The robotic surgical system 1 may vary the roll scaling factors (e.g., increase the roll scaling factor when the input device 46 is moved away from an aligned configuration and/or decrease the roll scaling factor when the input device 46 is moved towards the aligned configuration) until the input device 46 is at a predetermined offset or "trim" in a range of about 10° to about 45° (e.g., about 30°) relative to the input device 46. Once the input device 46 is at the predetermined offset relative to the input device 46, the robotic surgical system 1 ceases to vary the roll scaling factors to realign the input device 46 with the tool 20.

By allowing the input device 46 to remain offset from the tool 20 about one or more of the RPY axes, the position may allow the clinician to maintain a more comfortable hand and/or arm position during the surgical procedure. The predetermined offset may be the same or different about each of the RPY axes. For example, the predetermined offset may be in a range of about 5° to about 45° (e.g., about 15°) about each of the RPY axes. Alternatively, the predetermined offset about the roll axis may be about 30° and the predetermined offset about the pitch and yaw axes may be about 15°.

The predetermined offsets may be set by the robotic surgical system 1 or may be user selected. The predetermined offsets may be set by the robotic surgical system 1 based on the type of tool 20 connected to an arm 12 associated with the input device 46 and/or may be set by the robotic surgical system 1 based on the type of surgical procedure. It will be appreciated that as the predetermined offset increases, the control of the tool 20 may become more difficult. Accordingly, there may be limits to the maximum limits set for the user selected predetermined offsets.

Figure 4:
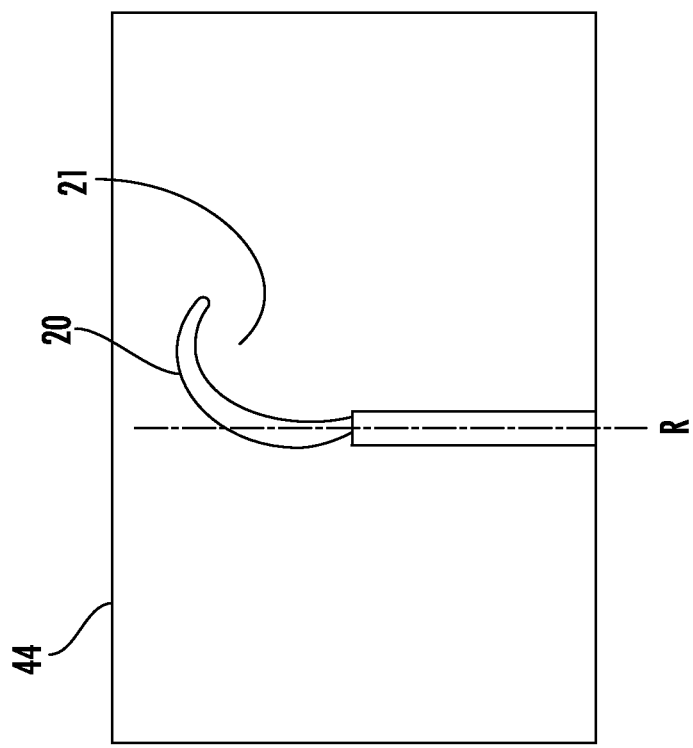
FIG. 4 is a view of the display device of FIG. 3 illustrating the representation of the tool of FIG. 3 rotated about 180° about a roll axis thereof.

Referring to FIGS. 3 and 4, it may be beneficial to "flip" one or more of the RPY axes if the misalignment is greater than a predetermined misalignment. One or more of the RPY axes is "flipped" when the aligned configuration about a respective axis is rotated 180° about the respective axis. A "flip" about a respective axis may be beneficial for control of a tool 20 when the tool 20 is asymmetrical or directional (e.g., a hook, curved scissors, curved dissector, etc.). For example, when a tool 20 is a hook with an opening 21 facing right as shown on the display device 44 in FIG. 3, the tool 20 can be "flipped" about the roll axis "R" such that the opening 21 faces left as shown on the display device 44 as shown in FIG. 4. The predetermined misalignment may be in a range of about 125° to about 195° (e.g., about 135°). Additionally or alternatively, a clinician may "flip" one or more of the RPY axes using a button, voice command, or GUI input. It is contemplated the robotic surgical system 1 may incorporate both a "trim" and a "flip" algorithm.

Additionally or alternatively, the robotic surgical system 1 may include a "snap" algorithm which is similar to the "flip" algorithm. A "snap" would occur when one or more of the RPY axes is misaligned greater than a predetermined misalignment. For example, when the roll axis "R" is misaligned about 45°, the trim of the roll axis "R" may snap to an offset of 45°. The snap algorithm may include a plurality of sequential offsets such that each time the particular RPY axes exceeds a predetermined misalignment, the respective RPY axis "snaps" to an offset associated with the predetermined misalignment. For example, the roll axis "R" may have predetermined snap points spaced 15, 30, or 45 degrees about the roll axis "R".

Referring back to FIG. 2, the input device 46 includes a button 47 to alter the scaling of one or more of the RPY scaling factors. For example, when the button 47 is depressed, the scaling factor about the roll axis "R" can be scaled up or scaled down to a predetermined value. Alternatively, when the button 47 is depressed, the input device 46 can be clutched out about the roll axis "R" while the other axes remain related to movement of the input device 46.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. A robotic surgical system or simulator comprising:
an input device rotatable about a first axis of rotation;
a display device including a representation of a surgical tool operably associated with the input device; and
a processing unit in communication with the input device and operatively associated with the representation of a surgical tool to rotate the representation of a surgical tool about a first axis of movement based on a scaled rotation of the input device about the first axis of rotation, the input device having an aligned configuration in which the input device is aligned with the representation of a surgical tool about the first axis of rotation, wherein when the input device is misaligned with the representation of a surgical tool about the first axis of rotation, the processing unit varies the scaled rotation of the input device about the first axis of rotation to return the input device to the first aligned configuration until the input device is misaligned about the first axis of rotation a first predetermined offset from the aligned configuration.

2. The robotic surgical system or simulator according to claim 1, the first predetermined offset is in a range of 5° and 45°.

3. The robotic surgical system or simulator according to claim 1, wherein the input device is rotatable about a second axis of rotation perpendicular to the first axis of rotation, wherein the processing unit is in communication with the input device and operably associated with the representation of a surgical tool to rotate the representation of a surgical tool about a second axis of movement based on a scaled rotation of the input device about the second axis of rotation, wherein, in the aligned configuration, the input device is aligned with the representation of a surgical tool about the second axis of rotation, and wherein when the input device is misaligned with the representation of a surgical tool about the second axis of rotation, the processing unit varies the scaled rotation of the input device about the second axis of rotation to return the input device to the aligned configuration until the input device is misaligned about the second axis of rotation a second predetermined offset from the aligned configuration.

4. The robotic surgical system or simulator according to claim 3, wherein the first predetermined offset is equal to the second predetermined offset.

5. The robotic surgical system or simulator according to claim 3, wherein the first predetermined offset is greater than the second predetermined offset.

6. The robotic surgical system or simulator according to claim 5, wherein the first predetermined offset is in a range of about 16° to about 45° and the second predetermined offset is in a range of about 5° to about 15°.

7. The robotic surgical system or simulator according to claim 3, wherein the input device is rotatable about a third axis of rotation perpendicular to the first and second axes of rotation, wherein the processing unit is in communication with the input device and operably associated with the representation of a surgical tool to rotate the representation of a surgical tool about a third axis of movement based on a scaled rotation of the input device about the third axis of rotation, wherein, in the aligned configuration, the input device is aligned with the representation of a surgical tool about the third axis of rotation, and wherein, when the input device is misaligned with the representation of a surgical tool about the third axis of rotation, the processing unit varies the scaled rotation of the input device about the third axis of rotation to return the input device to the aligned configuration until the input device is misaligned about the third axis of rotation a third predetermined offset from the aligned configuration.

8. The robotic surgical system or simulator according to claim 7, wherein the first predetermined offset is equal to each of the second predetermined offset and the third predetermined offset.

9. The robotic surgical system or simulator according to claim 7, wherein the first predetermined offset is greater than each of the second predetermined offset and third predetermined offset.

10. The robotic surgical system or simulator according to claim 9, wherein the second predetermined offset is greater than the third predetermined offset.

11. The robotic surgical system or simulator according to claim 1, wherein the first predetermined offset is selectable by a user.

12. The robotic surgical system or simulator according to claim 1, wherein the first predetermined offset is determined based on the representation of a surgical tool.

13. The robotic surgical system or simulator according to claim 1, wherein when the input device is misaligned with the representation of a surgical tool about the first axis of rotation by an amount greater than a predetermined misalignment, the aligned configuration is flipped 180° about the first axis of rotation.

14. A robotic surgical system or simulator comprising:
a surgical tool defining a first axis of movement;
a display device including a representation of the surgical tool operably associated with an input device;
an input device rotatable about a first axis of rotation, the input device having an aligned configuration in which the input device is aligned with the representation of the surgical tool about the first axis of rotation; and
a processing unit in communication with the input device and the display device, the processing unit being configured to:
rotate the representation of the surgical tool about a first axis of movement based on a scaled rotation of the input device about the first axis of rotation, and
wherein when the input device is misaligned with the representation of a surgical tool about the first axis of rotation, vary the scaled rotation of the input device about the first axis of rotation to return the input device to a first aligned configuration until the input device is misaligned about the first axis of rotation a first predetermined offset from the aligned configuration.

15. The robotic surgical system or simulator according to claim 14, wherein:
the input device is rotatable about a second axis of rotation perpendicular to the first axis of rotation; and
the processing unit is configured to:
rotate the representation of the surgical tool about a second axis of movement based on a scaled rotation of the input device about the second axis of rotation, wherein, in the aligned configuration, the input device is aligned with the representation of a surgical tool about the second axis of rotation; and
when the input device is misaligned with the representation of the surgical tool about the second axis of rotation, vary the scaled rotation of the input device about the second axis of rotation to return the input device to the aligned configuration until the input device is misaligned about the second axis of rotation a second predetermined offset from the aligned configuration.

16. The robotic surgical system or simulator according to claim 15, wherein:
the input device is rotatable about a third axis of rotation perpendicular to the first and second axes of rotation; and
the processing unit is configured to:
rotate the representation of the surgical tool about a third axis of movement based on a scaled rotation of the input device about the third axis of rotation, wherein, in the aligned configuration, the input device is aligned with the representation of a surgical tool about the third axis of rotation; and when the input device is misaligned with the representation of a surgical tool about the third axis of rotation, vary the scaled rotation of the input device about the third axis of rotation to return the input device to the aligned configuration until the input device is misaligned about the third axis of rotation a third predetermined offset from the aligned configuration.

17. The robotic surgical system or simulator according to claim 14, wherein the first predetermined offset is selectable by a user.

* * * * *